(12) United States Patent
Hordos et al.

(10) Patent No.: US 7,714,143 B1
(45) Date of Patent: May 11, 2010

(54) METHOD OF MAKING MONOAMMONIUM SALT OF 5,5'-BIS-1H-TETRAZOLE

(75) Inventors: Deborah L. Hordos, Troy, MI (US); Sean P. Burns, Almont, MI (US)

(73) Assignee: TK Holdings, Inc., Armada, MI (US)

( * ) Notice: Subject to any disclaimer, the term of this patent is extended or adjusted under 35 U.S.C. 154(b) by 0 days.

(21) Appl. No.: 12/080,099

(22) Filed: Mar. 31, 2008

Related U.S. Application Data

(60) Provisional application No. 60/921,445, filed on Mar. 31, 2007.

(51) Int. Cl.
*C07D 403/04* (2006.01)
*C06B 43/00* (2006.01)

(52) U.S. Cl. ........................ 548/250; 548/254

(58) Field of Classification Search ........................ None
See application file for complete search history.

(56) References Cited

U.S. PATENT DOCUMENTS

| | | | |
|---|---|---|---|
| 5,872,329 A | 2/1999 | Burns et al. | 149/36 |
| 6,210,505 B1 | 4/2001 | Khandhadia et al. | 149/36 |
| 6,214,139 B1 * | 4/2001 | Hiskey et al. | 149/36 |
| 6,306,232 B1 | 10/2001 | Khandhadia et al. | 149/22 |
| 6,570,022 B2 | 5/2003 | Naud et al. | 548/251 |
| 2008/0202654 A1 * | 8/2008 | Ganta et al. | 149/36 |

* cited by examiner

*Primary Examiner*—Fiona T Powers
(74) *Attorney, Agent, or Firm*—L.C. Begin & Associates, PLLC

(57) ABSTRACT

A method of forming monoammonium salt of 5,5'-bis-1H-tetrazole (BTA-1NH3) is presented comprising the steps of charging a mixing vessel with a solution of free BTA acid and distilled water, adding ammonium hydroxide in excess to obtain a pH of at least 9.5 and mixing the solution, and adding sulfuric acid cooled to 10-20 degrees Celsius to obtain a pH of at least 4.5 and mixing the solution. A gas generator 10 containing a gas generant 12 containing the BTA-1NH3 formed in accordance with the present invention is also presented. Gas generating systems 180 such as vehicle occupant protection systems 180, containing the gas generator 10, are also provided.

3 Claims, 1 Drawing Sheet

METHOD OF MAKING MONOAMMONIUM SALT OF 5,5'-BIS-1H-TETRAZOLE

CROSS-REFERENCE TO RELATED APPLICATIONS

Figure 1:
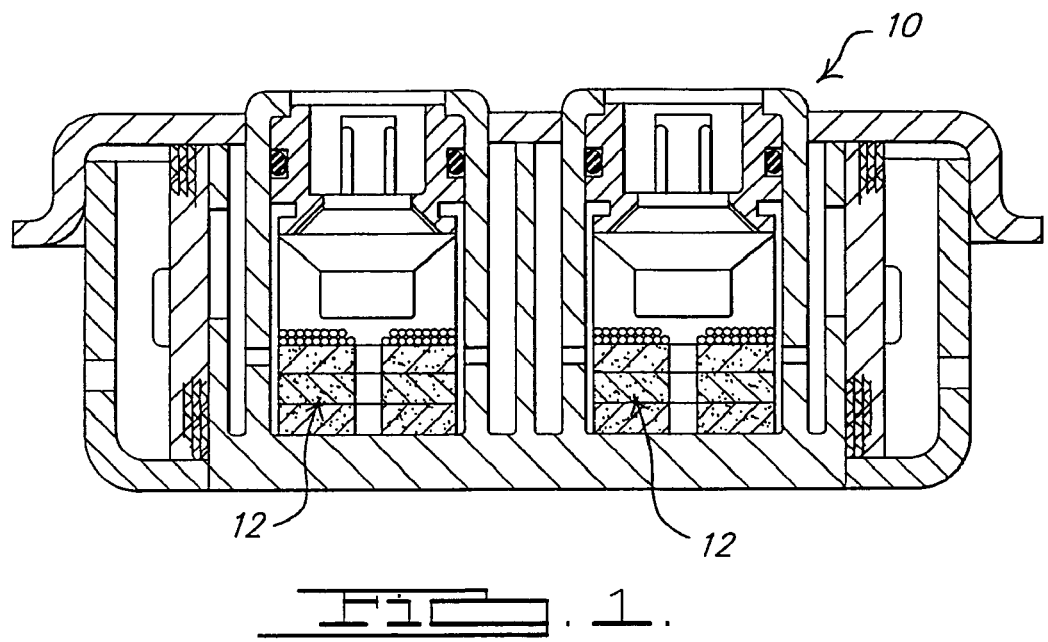

This application claims the benefit of U.S. Provisional Application Ser. No. 60/921,445 filed on Mar. 31, 2007.

TECHNICAL FIELD

The present invention relates generally to gas generating systems, and to gas generant compositions employed in gas generator devices for automotive restraint systems, for example.

BACKGROUND OF THE INVENTION

The monoammonium salt of 5,5'-bis-1H-tetrazole (BTA-NH3) has been found to be an excellent fuel for use in gas generants, in airbag inflators within vehicle occupant protection systems, for example. It has been found that the particle size and morphology of this fuel constituent nevertheless affects the performance of formulations that use it. It is believed that needle-like crystals of BTA-NH3 tend to bend and flex when exposed to a thermal gradient cycle spanning −40 C to 107 C. This effect creates aggressive ballistic results for propellant formulations that contain larger crystalline BTA-NH3 particles.

Smaller and amorphous BTA-NH3 particles apparently mitigate the detrimental effects of the bending and flexing of the larger needle-like structures. Accordingly, the size and shape of the BTA-NH3 particle has been found to be determinative of the stability of associated gas generant compositions with regard to temperature cycling or heat aging criteria. Furthermore, the improved bulk density provides advantageous packaging and storage requirements for BTA-NH3 when processed to produce particles having a desirable shape and size. When synthesized to the desired shape and size range, grinding to the desired size and shape is eliminated as a time critical step in the manufacturing process of BTA-NH3. Eliminating the grinding step also mitigates variability in combustion performance due to inconsistencies in the grinding process and therefore, inconsistencies in the average size of the BTA-1NH3.

SUMMARY OF THE INVENTION

The present invention resolves the aforementioned concerns by the discovery of a novel manufacturing process for the monoammonium salt of 5,5'-bis-1H-tetrazole(BTA-NH3). By first ammoniating BTA acid with ammonium hydroxide and then treating the solution with cold sulfuric acid and bringing the solution back to an acidic solution, the morphology/shape of the resulting monoammonium salt of BTA-NH3 can be controlled to be substantially smaller amorphous-shaped particles.

A gas generant incorporating the resultant fuel is yet another aspect of the present invention. A gas generating system incorporating the gas generant is also contemplated in accordance with the present invention.

DETAILED DESCRIPTION OF PREFERRED EMBODIMENTS

In a method of making BTA-NH3, it has been found that temperature and pH have a dynamic effect on the particle morphology of BTA-NH3. The experiments were conducted with free BTA acid in solution. Then the solution was ammoniated with ammonium hydroxide. Ammonium hydroxide was added in excess to obtain a pH of at least 9.5 and brought to a temperature of about 65 C. The pH was then adjusted with cold acid at about 5-20 degrees Celsius to a pH no greater than 4.5. Strong acids such as sulfuric acid or hydrochloric acid were used to lower the pH. The rapid precipitation of BTA-NH3 was observed in the pH range of about 5-7. The particle morphology is dramatically affected by the cold acidification step. Samples of BTA-NH3 prepared without acidification and with a slow cooling from 65 C to room temperature yielded a BTA-NH3 particle morphology of relatively large needle-like crystals measuring 80-100 microns. Samples of BTA-NH3 prepared with acidification yielded a BTA-NH3 particle morphology of relatively smaller amorphous crystals measuring an average 5 microns, with reduced needle formation. Using even colder sulfuric acid (less than or equal to 10 C) resulted in even less needle-like structure in the product yield. The present method resulted in a BTA-NH3 amorphous particle formation of 90% or greater percent yield.

Gas generant compositions (and methods of formulation) employing BTA-1NH3 of the present invention are described for example, and not by way of limitation, in U.S. Pat. Nos. 5,872,329, 6210,505, and 6,306,232, each incorporated by reference in their entirety.

The gas generant compositions of the present invention may be employed in known airbag inflators, gas generators, seatbelt pretensioners, gas generating systems, or other applications requiring the generation of gas.

Preliminary data indicates BTA-NH3 product yield having a particle size population of about 90% less than 10 microns. On the other hand, the needle-like structures were found to have particle sizes that were typically in the range of 75-100 microns in length. The smaller size resulted in favorable and improved ballistic performance wherein the fuel and the gas generant compositions were substantially less sensitive and less aggressive upon ignition after heat aging and thermal shock testing.

EXAMPLES

Example 1

A gas generant composition was formed with a monoammonium salt (BTA-1NH3) having typical needle-like crystals, as a fuel. The gas generant composition contained 72.53 wt % phase stabilized ammonium nitrate (PSAN), 27.22% BTA-1NH3, and 0.25% M5 fumed silica and was ground with ceramic media in a Sweco vibratory grinder for about 10 minutes. The resultant powder was then pressed into ¼" diameter by 0.125" thick tablets. Three known driver side inflators were loaded with 25.0 grams of the gas generant composition. The inflators were then sealed and subjected to the USCAR specification (thermal shock cycles between −40 C and +90 C wherein the temperature is alternatively cycled at each temperature for about 45 minutes). The first inflator was evaluated after 50 cycles and changes to the propellant were observed. The second inflator was evaluated after 100 cycles by activating the inflator. The ballistic performance was very aggressive and did not meet USCAR specification. After 200 cycles the third inflator was evaluated by activating the inflator. After 200 cycles, the ballistic performance was so aggressive that the inflator ruptured due to extremely high internal pressures. All inflators were tested or evaluated at +85 C. It is believed that pores or voids in the grain due to the bending or flexing of the needle-like structure of the fuel component results in aggressive ballistic behavior, whereas the ballistic behavior is controlled when using the amorphous structure of the same fuel component in accordance with the present invention.

In fact, the burn rate, ignition, and sustained burn of the gas generant composition improved with the amorphous structure when using BTA-1NH3 as a fuel. It is believed that the amorphous structure results in more intimate mixing with the PSAN thereby providing relatively favorable combustion data as compared to compositions employing the needle-like structure of the BTA-1NH3 fuel.

Example 2

In accordance with the present invention, a gas generant composition was formed as described in Example 3 with a mono-ammonium salt (BTA-1NH3) having amorphous-shaped crystals, as a fuel. The gas generant composition contained a mixture of about 73 wt % phase stabilized ammonium nitrate (PSAN) and about 27 wt % BTA-1NH3, was pressed into ¼" diameter by 0.125" thick tablets. Nine known driver side inflators (as used in Example 1) were loaded with 25.0 grams of the gas generant composition. The inflators were then sealed and subjected to heat aging for about 400 hours at 107 C. The same inflators were then subjected to the USCAR specification (thermal shock cycles between −40 C and +90 C wherein the temperature is alternatively cycled at each temperature for about 45 minutes).

Three inflators were evaluated at about +85 C by activating the inflators and measuring the pressure over time, from just prior to combustion at 0 seconds to 0.1 seconds over the combustion time. The average peak pressure was about 270 kPa during this time frame.

Three inflators were evaluated at about +23 C by activating the inflators and measuring the pressure over time, from just prior to combustion at 0 seconds to 0.1 seconds over the combustion time. The average peak pressure was about 245 kPa during this time frame.

Three inflators were evaluated at about −40 C by activating the inflators and measuring the pressure over time, from just prior to combustion at 0 seconds to 0.1 seconds over the combustion time. The average peak pressure was about 230 kPa during this time frame.

Example 3

In accordance with the present invention, a vessel was charged with a solution of free BTA acid. The solution was ammoniated with ammonium hydroxide and heated to about 65-70 C. Ammonium hydroxide was added in excess to obtain a pH of at least 9.5. The pH was then quickly adjusted with cold sulfuric acid at about 5-20 degrees Celsius to a pH no greater than 4.5. The rapid precipitation of BTA-NH3 was observed in the pH range of about 5-7. As shown in the examples given below, the particle morphology is dramatically affected by the cold acidification step. The bulk density of BTA-1NH3 was about 38 pounds per cubic foot. The tap density of BTA-1NH3 was about 30.5 pounds per cubic foot.

Example 4

A vessel was charged with a solution of free BTA acid. The solution was ammoniated with ammonium hydroxide and heated to about 65-70 C. Ammonium hydroxide was added in excess to obtain a pH of at least 9.5. A precipitate formed as the solution cooled. The bulk density of BTA-1NH3 was about 38 pounds per cubic foot. The tap density of BTA-1NH3 was about 30.5 pounds per cubic foot.

Example 5

A vessel was charged with a solution of 1.0 kg of free BTA acid. The solution was ammoniated with ammonium hydroxide in 5 L of distilled water. Ammonium hydroxide was added in excess to obtain a pH of at least 9.5 and the solution was concurrently heated to about 65-70 C. The solution was then hot charged to a chilled Ross Mixer. The pH was then adjusted to no more than 4.5 while cooling the solution by adding 33% cold sulfuric acid. The particles were analyzed by Laser Particle Size Analysis with the following results: the laser mean size was 5.9 microns; the 90 percentile size was 27.3 microns; the 50 percentile size was 5.5 microns; the 10 percentile size was 1.33 microns; and an exotherm of the fuel was found to be 273.03 C by differential scanning calorimetry (DSC) analysis.

Example 6

A vessel was charged with a solution of 1.0 kg of free BTA acid. The solution was ammoniated with ammonium hydroxide in 5 L of distilled water. Ammonium hydroxide was added in excess to obtain a pH of at least 9.5 and the solution was concurrently heated to about 65-70 C. Ice was then added to the mixer. The solution was then hot charged to a chilled Ross Mixer. The pH was then adjusted to no more than 4.5 while cooling the solution by adding 33% cold sulfuric acid. The particles were analyzed by Laser Particle Size Analysis with the following results: the laser mean size was 5.8 microns; the 90 percentile size was 32.19 microns; the 50 percentile size was 5.1 microns; the 10 percentile size was 1.11 microns; and an exotherm of the fuel was found to be 269.03 C by differential scanning calorimetry (DSC) analysis.

Example 7

A vessel was charged with a solution of 500 grams of free BTA acid and 13 L of distilled water. The solution was ammoniated with ammonium hydroxide. Ammonium hydroxide was added in excess to obtain a pH of at least 9.5. The solution was then hot charged to a chilled Ross Mixer. The mixture was maintained at a temperature of 10-15 C while cold 33% sulfuric acid solution was added while mixing to obtain a pH of about 4.5. The end mix temperature was about −5 C. The particles were analyzed by Laser Particle Size Analysis with the following results: the laser mean size was 4.5 microns; the 90 percentile size was 26.18 microns; the 50 percentile size was 3.925 microns; the 10 percentile size was 0.955 microns; and an exotherm of the fuel was found to be 284.64 C by differential scanning calorimetry (DSC) analysis.

Example 8

A vessel was charged with a solution of 500 grams of free BTA acid and 13 L of distilled water. The solution was ammoniated with ammonium hydroxide and heated to about 65-70 C. Ammonium hydroxide was added in excess to obtain a pH of at least 9.5. The solution was then hot charged to a chilled Ross Mixer. The mixture was maintained at a temperature of 10-15 C while 33% cold sulfuric acid solution was added while mixing to obtain a pH of about 4.5. The end mix temperature was −5 C. The particles were analyzed by Laser Particle Size Analysis with the following results: the laser mean size was 3.3 microns; the 90 percentile size was 16.6 microns; the 50 percentile size was 3.056 microns; the 10 percentile size was 0.906 microns; and an exotherm of the fuel was found to be 277.15 C by differential scanning calorimetry (DSC) analysis.

Example 9

A vessel was charged with a solution of 500 grams of free BTA acid and 13 L of distilled water. The solution was ammoniated with ammonium hydroxide and heated to about 65-70 C. Ammonium hydroxide was added in excess to obtain a pH of at least 9.5. The solution was then hot charged to a chilled Ross Mixer. The mixture was maintained at a temperature of 10-15 C while 33% cold sulfuric acid solution was added while mixing to obtain a pH of about 4.5. The end mix temperature was −5 C. The particles were analyzed by Laser Particle Size Analysis with the following results: the laser mean size was 2.7 microns; the 90 percentile size was 10.09 microns; the 50 percentile size was 2.709 microns; the 10 percentile size was 0.843 microns; and an exotherm of the fuel was found to be 278.24 C by differential scanning calorimetry (DSC) analysis.

Gas generant compositions of the present invention contain mono-ammonium salt of bis-(1(2)H-tetrazol-5-yl)-amine as a primary fuel at about 10-50 wt % of the total composition, and more preferably at about 20-35 wt % of the total composition. A secondary fuel may be selected from the group containing derivatives of bis-(1(2)H-tetrazol-5-yl)-amine, including its anhydrous acid and its acid monohydrate, metal salts of bis-(1(2)H-tetrazol-5-yl)-amine including the potassium, sodium, strontium, copper, boron, zinc salts of BTA-1NH3, and complexes thereof; azoles such as 5-aminotetrazole; metal salts of azoles such as potassium 5-aminotetrazole; nonmetal salts of azoles such as mono- or di-ammonium salt of 5, 5'-bis-1H-tetrazole; nitrate salts of azoles such as 5-aminotetrazole nitrate; nitramine derivatives of azoles such as 5-nitraminotetrazole; metal salts of nitramine derivatives of azoles such as dipotassium 5-nitraminotetrazole; nonmetal salts of nitramine derivatives of azoles such as mono- or di-ammonium 5-nitraminotetrazole and; guanidines such as dicyandiamide; salts of guanidines such as guanidine nitrate; nitro derivatives guanidines such as nitroguanidine; azoamides such as azodicarbonamide; nitrate salts of azoamides such as azodicarbonamidine dinitrate; and mixtures thereof. The total fuel component of the secondary fuel is generally provided at about 0.1-50 wt %, more preferably 0.1-30 wt %.

The gas generating compositions of the present invention also contain a first oxidizer selected from the group including nonmetal and metal nitrate salts such as ammonium nitrate, phase-stabilized ammonium nitrate, potassium nitrate, strontium nitrate; nitrite salts such as potassium nitrite; chlorate salts such as potassium chlorate; metal and nonmetal perchlorate salts such as potassium or ammonium perchlorate; oxides such as iron oxide and copper oxide; basic nitrate salts such as basic copper nitrate and basic iron nitrate, and mixtures thereof is provided. The first oxidizer is generally provided at about 0.1-80 wt % of the gas generant composition, and more preferably at about 10-70 wt %.

An optional secondary oxidizer may also be provided within the gas generant compositions, and is selected from the oxidizers described above, and when included is generally provided at about 0.1-50 wt %, and more preferably at about 0.1-30 wt %. The total combined oxidizer component is nevertheless only provided at about 0.1-80 wt % of the gas generant composition.

The gas generant composition may also contain an optional additive selected from the group including silicone compounds; elemental silicon; silicon dioxide; fused silica; silicones such as polydimethylsiloxane; silicates such as potassium silicates; natural minerals such as talc and clay; lubricants such as graphite powder or fibers, magnesium stearate, boron nitride, molybdenum sulfide; and mixtures thereof; and when included is generally provided at about 0.1-10%, and more preferably at about 0.1-5%.

An optional binder may be included in the gas generant composition and is selected from the group of cellulose derivatives such as cellulose acetate, cellulose acetate butyrate, carboxymethycellulose, salts of carboxymethylcellulose, carboxymethyl cellulose acetate butyrate; silicone; polyalkene carbonates such as polypropylene carbonate and polyethylene carbonate; and mixtures thereof, and when included is generally provided at about 0.1-10%, and more preferably at about 0.1-5%.

All percentages for the constituents described herein are presented as weight percents of a total gas generant weight.

As shown in FIG. 1, an exemplary inflator incorporates a dual chamber design to tailor the force of deployment of an associated airbag. In general, an inflator or gas generator 10 containing a primary gas generant 12 and BTA-1NH3 formed as described herein, may be manufactured as known in the art. U.S. Pat. Nos. 6,422,601, 6,805,377, 6,659,500, 6,749,219, and 6,752,421 exemplify typical airbag inflator designs and are each incorporated herein by reference in their entirety.

Figure 2:
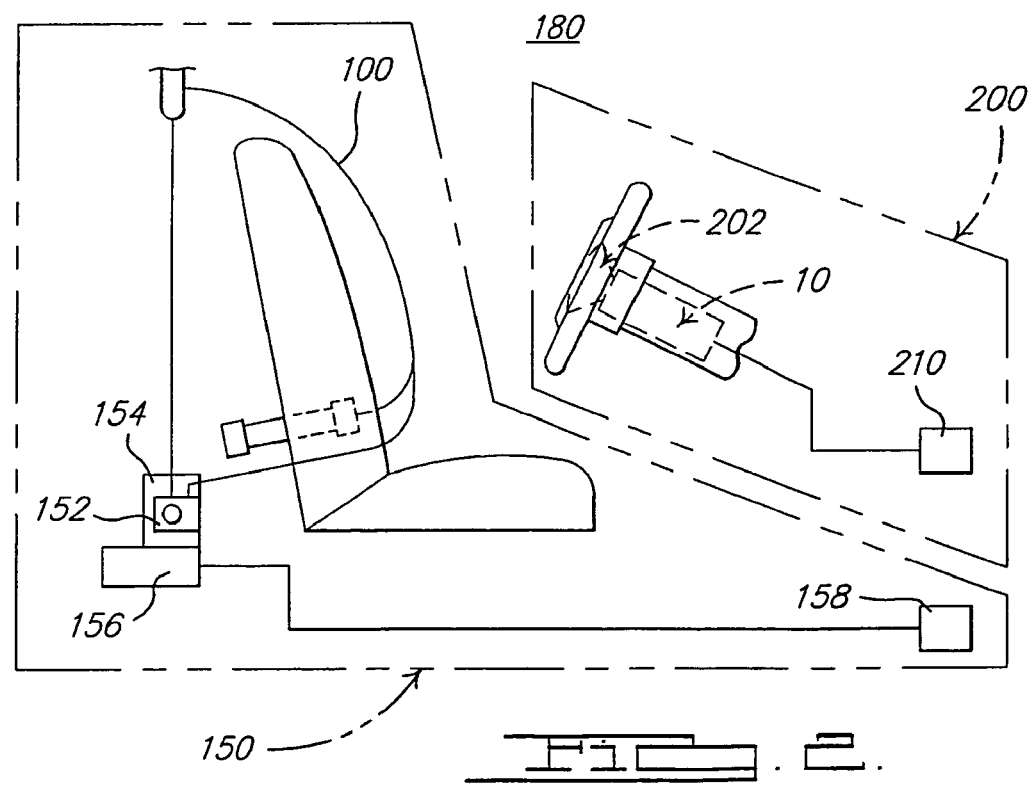

Referring now to FIG. 2, the exemplary inflator 10 described above may also be incorporated into an airbag system 200. Airbag system 200 includes at least one airbag 202 and an inflator 10 containing a gas generant composition 12 in accordance with the present invention, coupled to airbag 202 so as to enable fluid communication with an interior of the airbag. Airbag system 200 may also include (or be in communication with) a crash event sensor 210. Crash event sensor 210 includes a known crash sensor algorithm that signals actuation of airbag system 200 via, for example, activation of airbag inflator 10 in the event of a collision.

Referring again to FIG. 2, airbag system 200 may also be incorporated into a broader, more comprehensive vehicle occupant restraint system 180 including additional elements such as a safety belt assembly 150. FIG. 2 shows a schematic diagram of one exemplary embodiment of such a restraint system. Safety belt assembly 150 includes a safety belt housing 152 and a safety belt 100 extending from housing 152. A safety belt retractor mechanism 154 (for example, a spring-loaded mechanism) may be coupled to an end portion of the belt. In addition, a safety belt pretensioner 156 containing propellant 12 and autoignition 14 may be coupled to belt retractor mechanism 154 to actuate the retractor mechanism in the event of a collision. Typical seat belt retractor mechanisms which may be used in conjunction with the safety belt embodiments of the present invention are described in U.S. Pat. Nos. 5,743,480, 5,553,803, 5,667,161, 5,451,008, 4,558, 832 and 4,597,546, incorporated herein by reference. Illustrative examples of typical pretensioners with which the safety belt embodiments of the present invention may be combined are described in U.S. Pat. Nos. 6,505,790 and 6,419,177, incorporated herein by reference.

Safety belt assembly 150 may also include (or be in communication with) a crash event sensor 158 (for example, an inertia sensor or an accelerometer) including a known crash sensor algorithm that signals actuation of belt pretensioner 156 via, for example, activation of a pyrotechnic igniter (not shown) incorporated into the pretensioner. U.S. Pat. Nos.

6,505,790 and 6,419,177, previously incorporated herein by reference, provide illustrative examples of pretensioners actuated in such a manner.

It should be appreciated that safety belt assembly 150, airbag system 200, and more broadly, vehicle occupant protection system 180 exemplify but do not limit gas generating systems contemplated in accordance with the present invention.

The present description is for illustrative purposes only, and should not be construed to limit the breadth of the present invention in any way. Although the present inflator is described as preferably mounted on the driver side of a conventional automobile, the inflator might be applicable in other environments. Thus, those skilled in the art will appreciate that various modifications could be made to the presently disclosed embodiments without departing from the spirit and scope of the present invention.

What is claimed is:

1. A method of forming the monoammonium salt of 5,5'-bis-1H-tetrazole comprising the steps of:
    charging a mixing vessel with a solution of free 5,5'-bis-1H-tetraole acid and distilled water;
    ammoniating the solution to obtain a pH of at least 9.5 and mixing the solution; and
    acidifying the solution while cooling the solution to 5-20 degrees Celsius, to obtain a pH of at least 4.5 and precipitate a solid.

2. The method of claim 1 wherein the ammoniating step comprises adding ammonium hydroxide while heating the solution to about 65-70 C.

3. The method of claim 1 wherein the acidifying step comprises adding 33% sulfuric acid solution to the solution.

* * * * *